(12) United States Patent
Carlin et al.

(10) Patent No.: US 9,833,370 B1
(45) Date of Patent: Dec. 5, 2017

(54) MATTRESS WITH PATIENT RESTRAINT STORED INSIDE

(71) Applicant: MedPro US Inc., Islandia, NY (US)

(72) Inventors: Richard Carlin, Roslyn Estates, NY (US); Keith Ishida, Ontario, OR (US); Mark Krull, New Braunfels, TX (US)

( * ) Notice: Subject to any disclaimer, the term of this patent is extended or adjusted under 35 U.S.C. 154(b) by 157 days.

(21) Appl. No.: 14/661,264

(22) Filed: Mar. 18, 2015

Related U.S. Application Data (60) Provisional application No. 61/967,435, filed on Mar. 18, 2014.

(51) Int. Cl.
| | | |
|---|---|---|
| *A61G 7/05* | (2006.01) | |
| *A61F 5/37* | (2006.01) | |
| *A61G 1/044* | (2006.01) | |

(52) U.S. Cl.
CPC .......... *A61G 7/0504* (2013.01); *A61F 5/3769* (2013.01); *A61G 1/044* (2013.01); *A61G 7/05* (2013.01); *A61G 7/0507* (2013.01); *A61G 2200/16* (2013.01); *A61G 2200/32* (2013.01)

(58) Field of Classification Search
CPC . A61F 5/3769; A61F 5/3776; A61G 2200/16; A61G 2200/32; A61G 7/05; A61G 7/0504; A61G 7/0507; A61G 7/0519; A61G 7/052; A61G 7/0524; A61G 1/02; A61G 1/04; A61G 1/044; A61G 1/048
See application file for complete search history.

(56) References Cited

U.S. PATENT DOCUMENTS

| | | | | |
|---|---|---|---|---|
| 3,437,089 A | * | 4/1969 | Posey | A47D 15/008 128/875 |
| 4,132,229 A | * | 1/1979 | Morrison | A61F 5/3784 128/876 |
| 4,601,075 A | * | 7/1986 | Smith | A61G 1/044 128/870 |
| 4,757,811 A | * | 7/1988 | Clark | A61F 5/3769 128/876 |
| 4,979,520 A | * | 12/1990 | Boone, Jr. | A61G 1/01 128/870 |
| 4,998,308 A | * | 3/1991 | Farago | A61G 7/00 128/869 |
| 5,016,299 A | * | 5/1991 | Boulanger | A61G 7/0504 294/140 |
| 5,048,134 A | | 9/1991 | Dennill et al. | 5/82 R |
| 5,121,514 A | * | 6/1992 | Rosane | A61G 1/01 128/870 |

(Continued)

*Primary Examiner* — David E Sosnowski
*Assistant Examiner* — David R Hare (57) ABSTRACT

A patient restraining device is secured to a patient supporting structure, such as an ambulance cot, to more safely support a person's body during transport from one place to another. The device includes at least one sheet of fabric and connectors secured to the fabric. With the device fastened to an ambulance cot, either directly or via the ambulance cot mattress, a person is positioned on the cot mattress, and then the fabric is wrapped about the person's body, and the connectors are secured about the person's body. Among other things, the device may be used to stabilize the abdominal mass of a bariatric patient, and thereby safely increase the effective "patient capacity" of an otherwise conventional ambulance cot. When not in use, the device is stored in one or more storage cavities defined by the ambulance cot mattress.

16 Claims, 8 Drawing Sheets

(56) References Cited

U.S. PATENT DOCUMENTS

| | | | | |
|---|---|---|---|---|
| 5,150,487 A * | 9/1992 | Hemphill | ............... | A61G 1/044 |
| | | | | 5/625 |
| 5,154,185 A * | 10/1992 | Latimer | ............. | A61F 5/05833 |
| | | | | 128/DIG. 20 |
| 5,249,321 A * | 10/1993 | Graf | ..................... | A61G 7/0504 |
| | | | | 280/8 |
| 5,271,110 A * | 12/1993 | Newman | ................ | A61G 7/103 |
| | | | | 5/625 |
| 5,400,448 A * | 3/1995 | Zwickey | ............. | A61H 31/008 |
| | | | | 128/870 |
| 5,860,174 A * | 1/1999 | Failor | .................... | A61G 7/103 |
| | | | | 5/703 |
| 5,920,929 A * | 7/1999 | Hensley | ............... | A61G 7/1023 |
| | | | | 5/485 |
| 6,055,988 A * | 5/2000 | Perisho | ................. | A61G 1/044 |
| | | | | 128/869 |
| 6,135,114 A | 10/2000 | Elliott et al. | .................. | 128/869 |
| 6,363,936 B1 * | 4/2002 | McCormick | .......... | A61G 1/044 |
| | | | | 128/870 |
| 6,477,728 B1 | 11/2002 | Faz | ................................. | 5/625 |
| 6,568,009 B2 | 5/2003 | Linger et al. | .................... | 5/627 |
| 6,772,764 B2 * | 8/2004 | Chapman | ............... | A61G 1/044 |
| | | | | 128/846 |
| 7,610,640 B2 * | 11/2009 | Post | ..................... | A61G 7/0504 |
| | | | | 294/140 |
| 7,774,877 B2 * | 8/2010 | Kenalty | ................ | A61G 7/0504 |
| | | | | 5/494 |
| 7,904,979 B2 * | 3/2011 | Walke | .................. | A61G 7/0504 |
| | | | | 5/625 |
| 7,962,983 B2 * | 6/2011 | Keesaer | ................... | A61G 1/01 |
| | | | | 5/627 |
| 7,975,330 B2 * | 7/2011 | Receveur | .......... | A61G 7/05784 |
| | | | | 5/691 |
| 8,365,740 B1 * | 2/2013 | Ishida | .................. | A61F 5/3776 |
| | | | | 128/869 |
| 8,667,629 B2 * | 3/2014 | Mohr | ..................... | A61G 1/044 |
| | | | | 5/625 |
| 2009/0038076 A1 | 2/2009 | Giduck | ............................ | 5/627 |
| 2009/0094743 A1 * | 4/2009 | Tanaka | ................ | A61G 7/0504 |
| | | | | 5/81.1 T |
| 2012/0118300 A1 * | 5/2012 | Wysozki | ................ | A61F 5/3776 |
| | | | | 128/876 |
| 2012/0272451 A1 * | 11/2012 | Haskell | .................... | A61G 1/01 |
| | | | | 5/628 |

* cited by examiner

MATTRESS WITH PATIENT RESTRAINT STORED INSIDE

CROSS-REFERENCE TO RELATED APPLICATION

Disclosed herein is subject matter that is entitled to the filing date of U.S. Provisional No. 61/967,435, filed Mar. 18, 2014.

FIELD OF THE INVENTION

The present invention relates to methods and apparatus for restraining a person, and in a preferred application, to restraining methods and apparatus for bariatric patients resting on top of an ambulance cot mattress.

BACKGROUND OF THE INVENTION

On various occasions and in various situations, a need exists to transport a person by ambulance cot, stretcher, rolling hospital bed, or other such device. For the most part, these devices have been built according to generally accepted standards, taking into account factors that include the nominal size of patients.

In recent times, people are increasingly becoming obese, and more obese than ever. At some point, obese people reach a size that makes it dangerous (to them and the people doing the transporting) for them to be transported by traditional means. In other words, many of the currently existing ambulance cots, stretchers, etc. are not large enough to accommodate a growing segment of the population.

One possible solution to this problem is to introduce larger ambulance cots, but this would be difficult and costly to implement. For example, larger ambulance cots may not fit into existing ambulances or may not fit through existing doorways. Also, replacing all existing ambulance cots would take time.

Another possible solution to this problem is to provide a supplemental platform that essentially rests on top of a traditional ambulance cot. However, this solution would encounter problems similar to those discussed above with respect to introducing larger ambulance cots, and may do nothing to reduce the likelihood of the cot tipping over.

In other words, there exists a need for a practical solution to transporting people that are too big for existing patient supporting structures. Some possible solutions to this problem are disclosed in U.S. Pat. No. 8,365,740 to Ishida, but room for continued improvement remains.

SUMMARY OF THE INVENTION

One aspect of the present invention is to provide a mattress that defines at least one internal storage cavity, and a patient restraint alternatively stored inside the cavity and deployed from the cavity for use.

In a preferred application, the mattress is an ambulance cot mattress that defines opposite left side and right side cavities, and the patient restraint includes left side and right side restraints that are selectively connected to one another. Each restraint includes a sheet of fabric and connectors secured to the sheet of fabric. In use, the device is fastened to the ambulance cot frame, either directly or via the mattress, and after the person is positioned on the patient supporting structure, the fabric is wrapped about the person's body, especially the abdominal mass, and the left side connectors are secured to respective right side connectors to form a snug "wrap" about the person's body.

In this preferred application, the present invention device "upgrades" an ambulance cot to accommodate bariatric people that would not otherwise fit safely onto the cot. In doing so, the present invention does not change the basic dimensions of the cot and/or interfere with the operational parameters of the cot. Many features and/or advantages of the present invention will become apparent from the more detailed description that follows.

BRIEF DESCRIPTION OF THE FIGURES OF THE DRAWING

With reference to the Figures of the Drawing, wherein like numerals represent like parts throughout the several views.

DETAILED DESCRIPTION OF A PREFERRED EMBODIMENT

Figure 1:
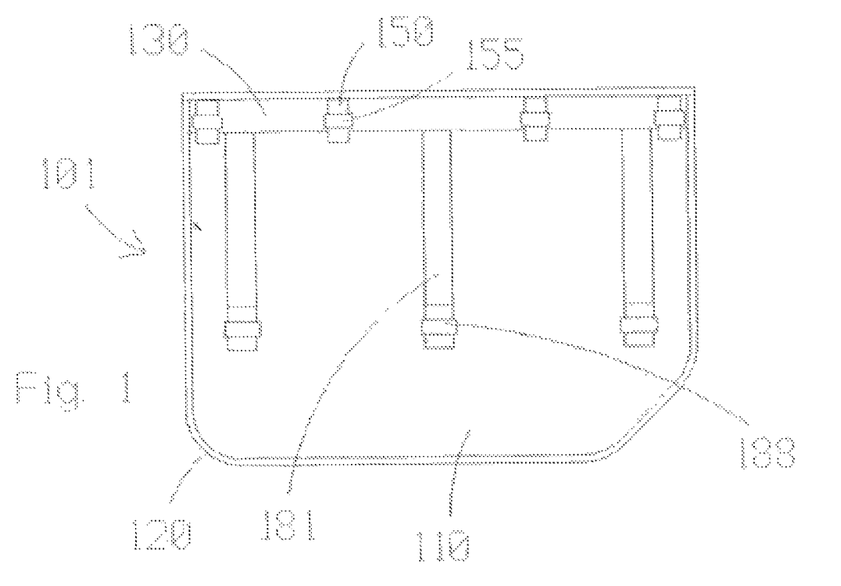
FIG. 1 is an exterior plan view of a first patient restraining panel constructed according to the principles of the present invention.
Figure 2:
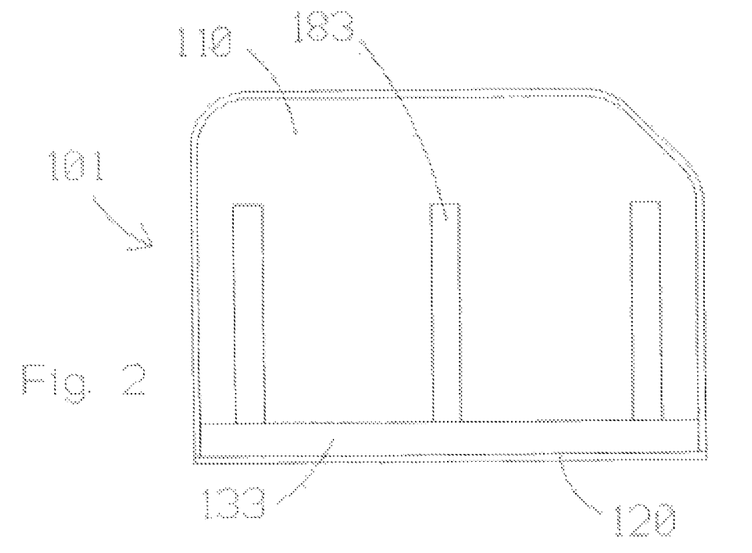
FIG. 2 is an opposite, interior plan view of the patient restraining panel of FIG. 1.
Figure 3:
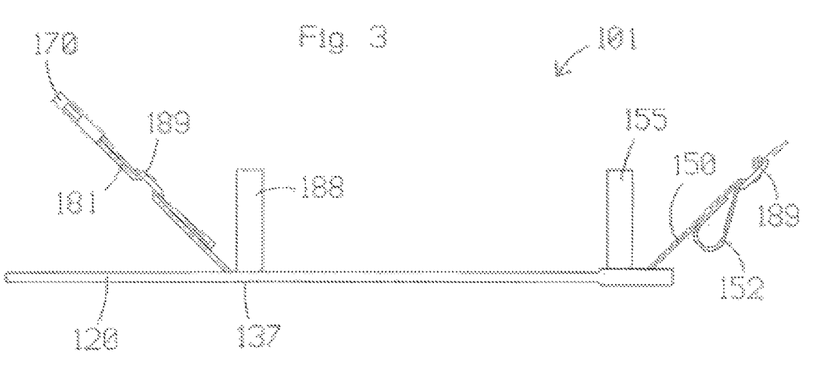
FIG. 3 is a side view of the patient restraining panel of FIG. 1.
Figure 4:
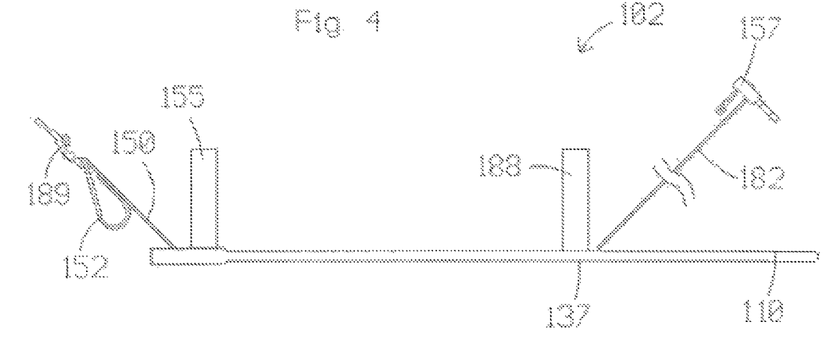
FIG. 4 is a side view of a second patient restraining panel constructed according to the principles of the present invention.

FIGS. 1-3 show a first patient restraining panel 101 constructed according to the principles of the present invention, and FIG. 4 shows a second patient restraining panel 102 constructed according to the principles of the present invention. With the exception of complementary male and female buckle members on respective panels 101 and 102, the panels 101 and 102 are mirror images of one another. The panels 101 and 102 cooperate with one another to define a patient restraining apparatus (designated as 100 in FIG. 11) and cooperate with a patient supporting structure (designated as 90 in FIGS. 5 and 10-11) to define a patient stabilizing system for temporarily, safely, and comfortably limiting movement of a body portion of a human patient. In a preferred application, the apparatus 100 limits movement of the potentially destabilizing abdominal mass of a bariatric person relative to an ambulance cot 90. In certain respects, the panels 101 and 102 and their operation are comparable to items disclosed in U.S. Pat. No. 8,365,740 to Ishida, which is incorporated herein by reference to supplement this description.

FIGS. 1-2 show respective exterior and interior sides of the panel 101 in an unfurled configuration. Generally speaking, each panel 101 and 102 includes a respective sheet of fabric 110, opposing pairs of reinforcing straps 130 and 133 secured to one another along a base edge of the fabric 110, anchor straps 150 disposed on the exterior side of the fabric 110 and secured between the reinforcing straps 130 and 133, and respective patient restraining straps 181 and 182 disposed on the exterior side of the fabric 110 and secured both between the reinforcing straps 130 and 133 and to respective reinforcing straps 183 disposed on the opposite, interior side of the fabric 110.

Each sheet of fabric is preferably a sheet of Phifertex mesh that measures three feet in length and two feet across (with one rounded corner having a radius of curvature of three inches and one clipped or chamfered corner). The mesh comprises longitudinally extending elements that are spaced one-sixteenth of an inch apart from one another, and laterally extending elements that are spaced one-eighth of an inch apart from one another. An advantage of the mesh is that it does not fully encapsulate a patient's body, and it allows a caretaker to see through the fabric 110 and thereby continue monitoring conditions of the patient's body (e.g. bleeding). Additional advantages of using a fabric such as Phifertex are that the material is durable, flexible, inelastic, washable and reusable. Although Phifertex mesh is the preferred material, persons skilled in the art will recognize that alternative embodiments of the present invention may be made with other known suitable materials.

Persons skilled in the art will also recognize that alternative embodiments may be made of different sizes. Accordingly, the panels 101 and 102 may alternatively be described in terms of size ranges, including, for example, two feet to four feet in length and twenty inches to thirty inches in width. Also, the size may be described in terms of minimums, including, for example, at least two feet long and at least twenty inches wide. All dimensions are provided for reference purposes, and none of them should be construed as defining or limiting the scope of the invention.

First and second reinforcing straps 130 and 133 are disposed on respective first and second sides of the sheet 110. The reinforcing straps 130 and 133 are preferably two and one-half inch wide Nylon webbing. The straps 130 and 133 are aligned with one another to extend lengthwise along a base edge of the sheet 110 and sewn to one another. Secured therebetween are the sheet 110, the ends of the anchor straps 150, the ends of the connector straps 181 or 182, and the ends of the reinforcing straps 183. A trim element 120 is secured about the perimeter of the fabric sheet 110 (and any adjacent edges of the other components), so there are no exposed edges. The trim element 120 is preferably a one-inch wide strip of rugged cloth that is folded in half over the edge of the fabric 110, and sewn to itself with the other components sandwiched therebetween.

At four locations along the length of each panel 101 and 102, anchor straps or fasteners 150 are disposed on the exterior side 112 of the sheet of fabric 110. Each anchor strap 150 is preferably a one and one-half inch wide strap of Nylon webbing. As shown in FIGS. 3-4, each anchor strap 150 has a first end anchored to a respective sheet 110, and an opposite, second end inserted through a buckle member 189 and then doubled back and sewn to itself to prevent removal from the buckle member 189. The buckle member 189 may be secured in place on the second end of the anchor strap 150, or selectively slidable along the second end of the anchor strap 150 to adjust the operational length of the strap 150. A second strap 152 has a first end that is sewn to an intermediate portion of the anchor strap 150, and a distal second end that is selectively routed through the buckle member 189 to form a closed loop (for reasons discussed below).

A separate lashing strap 155 is preferably provided for each anchor strap 150 (and associated second strap 152). Each lashing strap 155 has a middle portion that is secured to a respective reinforcing strap 130 at a point of intersection with a respective anchor strap 150. Each lashing strap 155 includes a first distal end that is provided with loop-type fasteners and an opposite, second distal end that is provided with hook-type fasteners that face toward the loop-type fasteners when the ends of the strap 155 overlap. Each lashing strap 155 releasably secures a respective anchor strap 150 (and second strap 152) in a folded storage configuration (as shown in FIG. 1). The ends of the lashing strap 155 are separated from one another to free the associated anchor strap 150 (and second strap 152) for deployment and use, as further described below.

At three locations along the length of each panel 101 and 102, the sheet of fabric 110 is sandwiched and sewn in place between respective patient restraining or connector straps or strap segments 181 or 182 and respective interior reinforcing straps 183, all of which in turn, are sandwiched and sewn in place between the reinforcing straps 130 and 133. Each patient restraining strap 181 and 182 is preferably a two inch wide strap of conventional Nylon webbing. The straps 181 or 182 are stitched in place along the entire length of respective reinforcing straps 183. Each patient restraining strap 181 and 182 may be described in terms of (1) a first portion that overlaps a respective strap 183 and is sewn thereto with the sheet of fabric 110 therebetween, and a second portion that is a loose or distal end.

Near the juncture between the two above-described portions of each strap 181 and 182, a respective lashing strap 188 is disposed directly beneath the strap 181 or 182 and sewn in place between the strap 181 or 182 and a respective strap 183. The ends of each lashing strap 188 are provided with respective mating hook-and-loop type fasteners to releasably secure a respective patient restraining strap 181 or 182 in a folded-up storage configuration against the sheet of fabric 110, as shown in FIG. 1. The ends of the lashing strap 188 are separated from one another to free the associated patient restraining strap 181 or 182 for deployment and use. When fully deployed in a longitudinally extending direction, each patent restraining strap 181 or 182 extends eighteen inches beyond the edge of the sheet of fabric 110. This maximum extent of deployment may alternatively be described as at least twelve inches.

As shown in FIG. 3, a distal end of each restraining strap (or connector strap) 181 is inserted through a respective slide buckle 189, and then through a respective female buckle member or end connector 170, and then doubled back against itself and inserted back through the slide buckle 189 and then folded over and stitched to itself. As a result, both the operational length of the patient restraining straps 181 and the positions of the buckles 170 along the patient restraining straps 181 are adjustable. The female buckle member 170 is a conventional part that mates with a corresponding male buckle member 157. As shown in FIG. 4, a distal end of each restraining strap 182 is inserted through a respective male buckle member or end connector 157 and then folded over and stitched to itself to prevent removal from the male buckle member 157.

On alternative embodiments of the invention, the disclosed buckle members may be replaced by alternative arrangements. For example, different types of conventional buckles, clasps, fasteners, hooks, latches and the like may be substituted for the disclosed buckle members. Alternatively, a belt buckle may be provided on one strap and maneuvered into engagement with any of a series of holes formed at longitudinal intervals in an opposing strap. Also, hook-and-loop fasteners may be disposed on the straps and/or the fabric to releasably secure the straps in place. Persons skilled in the art will also recognize that different sized straps and/or types of straps may be used without departing from the scope of the present invention.

Persons skilled in the art will also recognize that other sizes and/or types of straps may be used on alternative embodiments without departing from the scope of the present invention. Furthermore, the reinforcing straps 130 and 133 and/or the patient restraining straps 181 and 182 and reinforcing straps 183 may be secured in placing using additional or alternative means, including adhesives, bonding agents, or rivets or other fasteners, for example. On the preferred embodiment, these straps are glued in place relative to one another, and then sewn in place.

Figure 5:
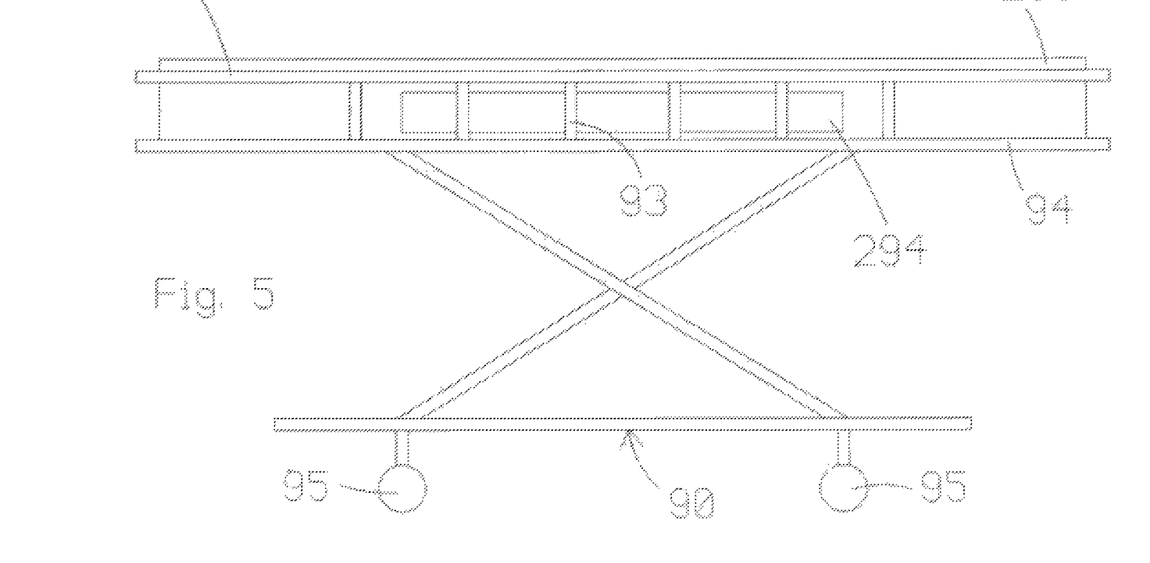
FIG. 5 is a side view of an otherwise conventional ambulance cot supporting an ambulance cot mattress constructed according to the principles of the present invention.

FIG. 5 is a diagrammatical representation of an otherwise conventional ambulance cot 90 that is supporting an ambulance cot mattress 291 constructed according to the principles of the present invention. The mattress 291 has a length that is measured from a head end to a foot end (right to left in FIGS. 5 and 6), and a width that is measured laterally from a left side to a right side (perpendicular to the drawing sheet of FIGS. 5 and 6). Left and right rails 92 are disposed along respective left and right sides of the mattress 291. Posts 93 are interconnected between respective rails 92 and a relatively lower base structure 94. The rails 92, posts 93 and base structure 94 cooperate to define a mattress frame or support structure that is rollably supported on wheels 95.

Figure 6:
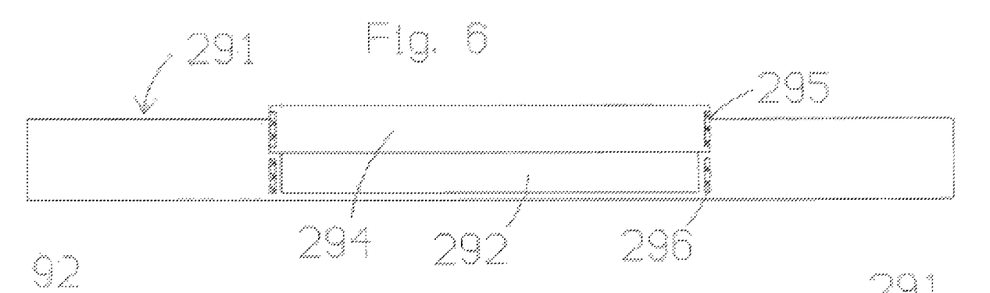
FIG. 6 is a side view of just the ambulance cot mattress of FIG. 5.

As shown in FIG. 6, the cot mattress 291 defines side pockets or cavities 292 along each side of the mattress 291 (one of which is visible in FIG. 6). Each pocket or cavity 292 is essentially a lined void inside the foam or other padding material disposed inside the mattress 291, and is sized and configured to receive and retain a respective folded up panel 101 or 102 for storage when not in use. The padding material is preferably removed from a lower portion of the mattress 291, so that padding material remains in place above the pockets 292 for maximum patient comfort.

Access to the pockets 292 is selectively blocked by respective flaps 294 on respective sides of the mattress 291. Each flap 294 is connected to a respective side of the mattress 291 above a respective pocket 292 and pivots downward to cover or close off a respective pocket 292. Hook-type Velcro fasteners 295 are secured to the flaps 294 and engage with respective loop-type Velcro fasteners 296 secured to the sides of the mattress 291 adjacent the pockets 292, to releasably secure the flaps 294 in closed positions relative to respective pockets 292 regardless of whether or not the panels 101 and 102 are in respective pockets 292.

Figure 7:
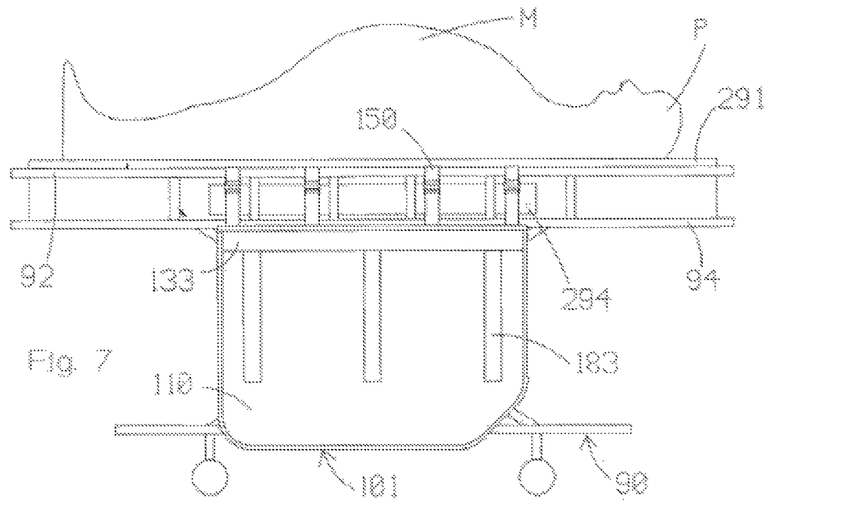
FIG. 7 is a side view of a bariatric person lying supine on top of the ambulance cot of FIG. 5, with the patient restraining panels of FIGS. 1 and 2 secured to respective fasteners on respective sides of the ambulance cot.
Figure 8:
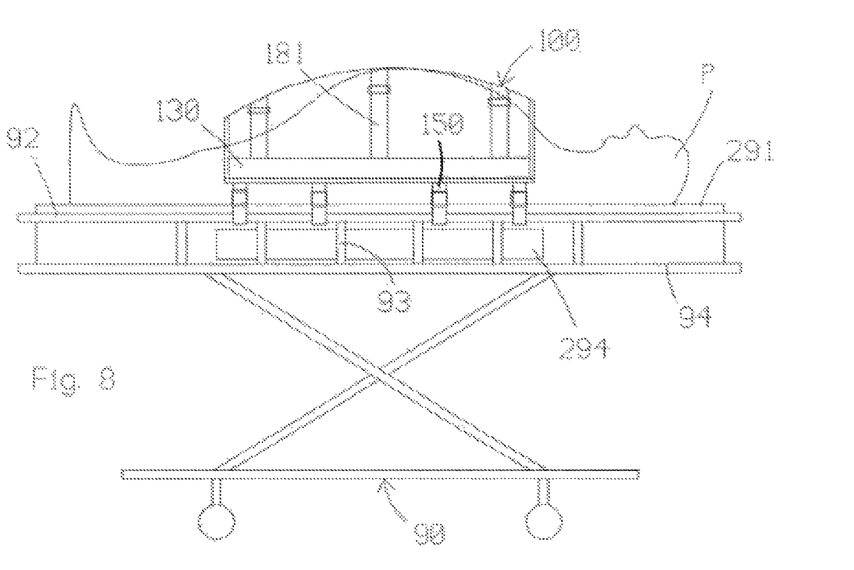
FIG. 8 is a side view of the patient restraining panels wrapped about the bariatric person of FIG. 7 and secured to one another to stabilize the abdominal mass of the bariatric person.

FIGS. 7 and 8 show the panel 101, and to a lesser extent the panel 102, of the apparatus 100 connected to respective sides of the ambulance cot 90 of FIG. 5, via the anchor straps 150 (and the associated second straps 152). In this regard, each second strap 152 is routed around a side of the rail 92 opposite a respective anchor strap 150, and then routed through a respective buckle member 189 and cinched in place.

A patient, in this case a bariatric person P, is positioned on top of the mattress 291. Then the panels 101 and 102 are wrapped about the person's torso (and one over the top of the other if need be), and the patient restraining straps 181 and 182 are maneuvered about the sheets of fabric 110 and the person P. Then the patient restraining straps 181 and 182 are interconnected to safely and comfortably secure the person P to the patient supporting structure 90. The buckle slides 189 may be adjusted along the straps 181 to ensure that the person P is properly and comfortably stabilized on the cot 90. Typically, the person's arms are kept outside the sheets of fabric 110 (for ease of illustration, the arms of the person P are not shown in FIGS. 7-8). The device 100 restrains the person P in a manner that does not compromise breathing, and that typically lowers the anxiety of the person P.

The patient supporting structure 90 is sized and configured to safely support a person of a maximum size, and the person P is greater than that maximum size. More specifically, the person P has an excessively large abdominal section M that makes placement on the cot 90 uncomfortable and potentially unsafe for both the person P and the personnel responsible for handling the cot 90. In this regard, the large abdominal mass M of the person P is capable of shifting significantly when the person P is positioned on the cot 90 without the device 100. Any such shift is capable of placing the person P in an awkward and potentially painful position, as well as tipping the cot 90 or putting significant strain on the people handling the cot 90. When implemented as shown in FIG. 9, the device 100 keeps the abdominal mass M over center and generally stationary relative to the cot 90, so the person P feels safe, and the cot 90 remains stable and secure.

Figures 9, 11:
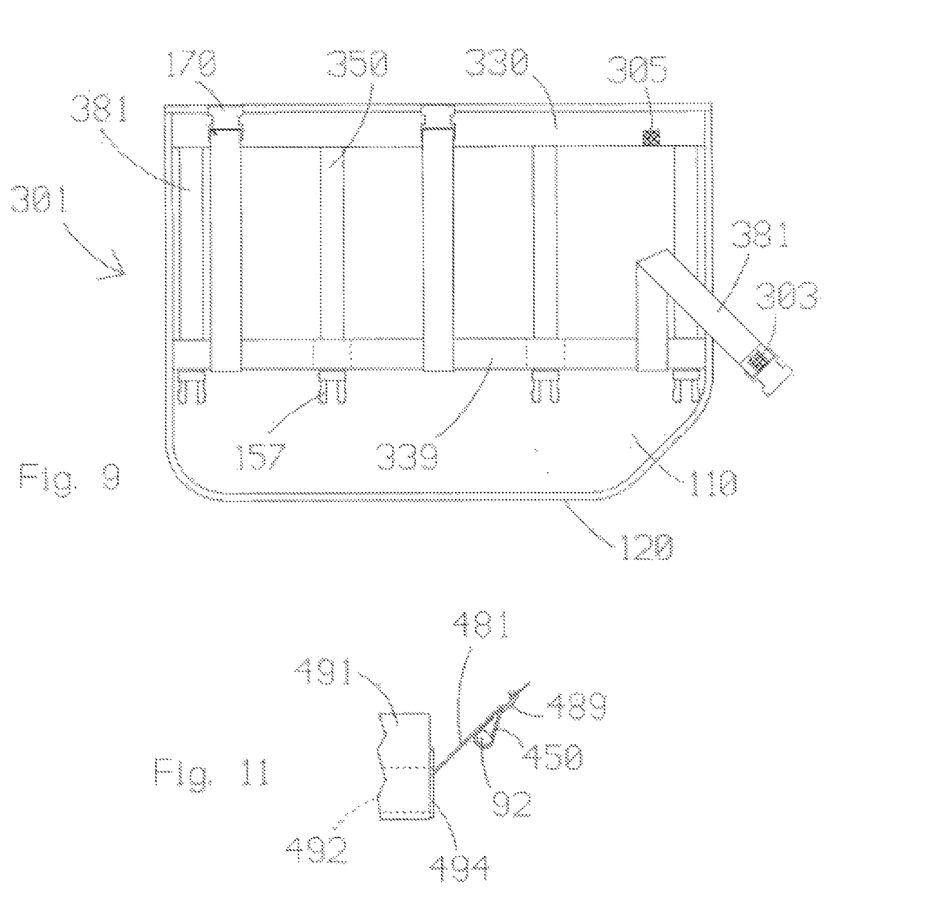
FIG. 9 is an exterior plan view of an alternative embodiment patient restraining panel constructed according to the principles of the present invention.
FIG. 11 is a fragmented enlarged end view of a portion of the device of FIG. 10 secured about an ambulance cot rail.

FIG. 9 shows an alternative panel 301 constructed according to the principles of the present invention and suitable for use in place of the panel 101. As with the preferred embodiment 100, the panel 301 is designed to cooperate with a second panel (not shown) that is a mirror image of the panel 301, except for respective male and female buckle members. As suggested by the common reference numerals, the panel 301 is similar in many respects to the panel 101, and the panels 301 and 101 are identical except as noted below. Moreover, when in use, the panel 301 is functionally equivalent to the panel 101. However, the panel 301 is designed to occupy a different configuration for storage purposes.

A retainer strap 339 is spaced apart from and extends parallel to the reinforcing straps 130 and is sewn intermittently to the fabric 110 and/or a similar strap on an opposite side of the fabric 110, leaving segments that cooperate with the fabric 110 to define passages or slots. Dashed lines show where stitching bounds the edges of the slots near the center of the panel 301, and the other slots, near the edges of the panel 301, are defined by stitching associated with the border 120 and the patient restraining straps 381. Each anchor strap 350 is sized and configured to extend through a respective slot with a respective buckle member discouraging withdrawal from the slot.

Hook-type Velcro fasteners 303 are mounted on each patient restraining strap 381 proximate a respective buckle member 170, and mating loop-type Velcro fasteners 305 are mounted on the reinforcing strap 330. The restraining straps 381 are sized and configured to fold onto themselves and extend to the reinforcing strap 330 in such a manner that the Velcro fasteners 303 and 305 engage one another and releasably hold the restraining straps 381 in the overlapped positions shown to the left in FIG. 9.

When the panel 301 is arranged as shown in FIG. 9 (except for the right patient restraining strap 381), the panel 301 will lie relatively flat beneath a conventional ambulance cot mattress. In the alternative, this arrangement of the panel 301 may be folded one or more times into a relatively flat configuration for placement in the cot mattress pockets 292 shown in FIG. 6.

Figure 10:
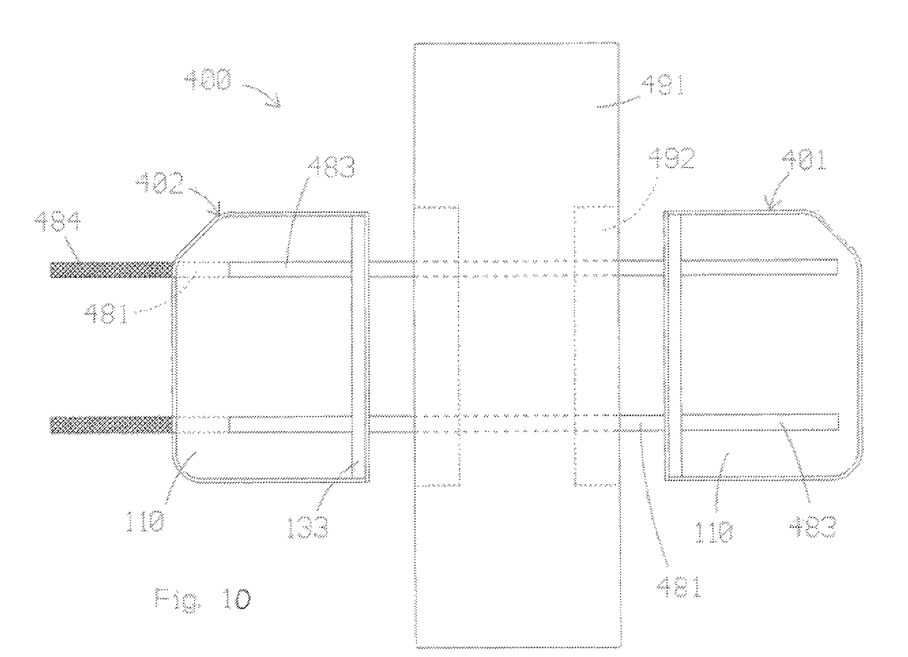
FIG. 10 is a top view of a combination ambulance cot mattress and patient restraining device constructed according to the principles of the present invention and suitable for use on the ambulance cot of FIG. 5.

FIGS. 10-11 show another embodiment 400 of the present invention. This embodiment 400 includes a cot mattress 491 having side pockets 492 like those described above with reference to FIG. 6, and having first and second panels 401 and 402 integrally connected to both the cot mattress 491 and one another. In many respects, the construction of the panels 401 and 402 is similar to the construction of the panels 101 and 102, and they should be considered identical except as noted below. Also, the mattress 491 is sized and configured to be substituted for the mattress 291 shown in FIG. 5.

First and second sheets of Phifertex fabric 110 are sandwiched and secured between respective reinforcing straps 130 and 433 and between patient restraining straps 481 and respective reinforcing straps 483. Each patient restraining strap 481 has a first end portion that is integrated into the first panel 401, an opposite, second end portion that is integrated into the second panel 402, and an intermediate portion that spans and is secured to the mattress 491. A distal end segment of each restraining strap 481 extends beyond the second panel 402, and hook-type Velcro fasteners 484 are secured to the inwardly facing side of each distal end segment. Mating loop-type Velcro fasteners (not shown) are secured to the outwardly facing side of the end portions of the patient restraining straps 481 on the first panel 401. When the panels 401 and 402 are wrapped about a patient's abdomen, the Velcro fasteners on the opposite ends of the patient restraining straps 481 are secured to one another to hold the patient's abdomen in place.

FIG. 11 shows one of the patient restraining straps 481 emanating from the mattress 491 and connected to an ambulance cot rail 92. A flap or cover 494 on the mattress 491 is notched to accommodate passage of each patient restraining strap 481 when the cover 494 is closed relative to the pocket 492. A fastener or anchor strap 450 has a first end portion that is sewn to the patient restraining strap 481, an intermediate portion that is looped about the ambulance cot rail 92, and an opposite, second end portion that is inserted through a slide buckle 489 this is disposed on a proximate portion of the patient restraining strap 481. This arrangement anchors each panel 401 and 401 (and the apparatus 400) to the ambulance cot 90.

FIGS. 12-15 show still another embodiment 500 of the present invention. This embodiment 500 may be described in terms of an ambulance cot mattress 591 in combination with at least one patient restraining panel or restraint 501 or 502, and preferably opposite left and right patient restraining panels or restraints 501 and 502.

In many respects, the mattress 591 is similar to a commercially available bolstered mattress product that is distributed by Stryker EMS, a company having a physical address in Portage, Mich., and having a home page internet address of ems.stryker.com. In terms of size, shape, and materials, the mattress 591 should be considered identical to this commercially available Stryker product except where otherwise noted.

In many respects, the patient restraints 501 and 502 are similar to the restraints 101 and 102, and are also similar to opposite left and right portions of a commercially available patient restraint product that is distributed by BEAR-iatrics Inc., a company having a physical address in Ontario, Oreg., and having a home page internet address of beariatrics.com. In the absence of information to the contrary, the patient restraints 501 and 502 should be considered identical to the restrains on this commercially available product and/or to the restraints 101 and 102 described above. In addition, reference is made to the restraints disclosed in U.S. Pat. No. 8,365,740 to Ishida, which was incorporated by reference earlier in this description.

Figure 15:
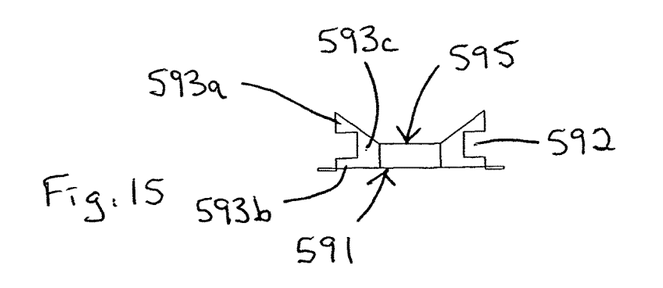
FIG. 15 is a sectioned end view of the combination of FIG. 14.

Like the mattress 291, the mattress 591 has a mattress body that defines left side and right side pockets or cavities 592 sized and configured to receive and retain respective restraints 501 and 502 when not in use. As shown in FIG. 15, respective elements of foam or other conventional mattress padding material 593a, 593b, and 593c is disposed above, below, and inboard of each cavity 592. The foam is contained within a fabric skin or upholstered exterior, which among other things, defines an upwardly facing body supporting surface 595. Opposite each padding element 593c, a zipper 596 extends along the side of each cavity 592 and operates in conventional fashion to open and close the cavity 592.

Figure 12:
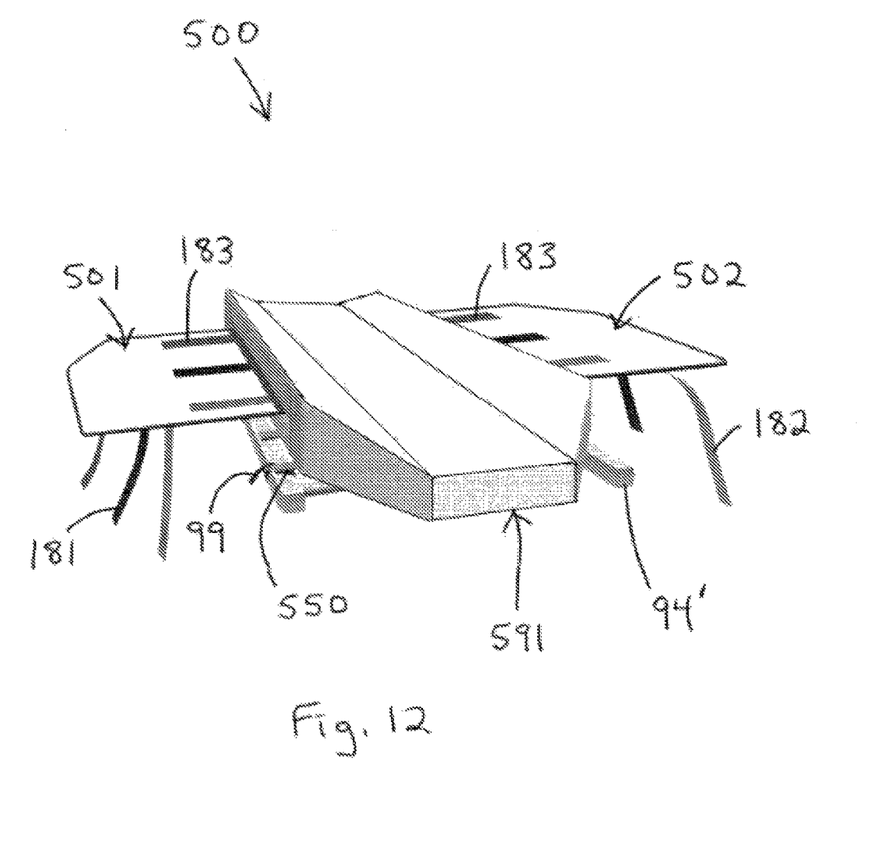
FIG. 12 is a perspective view of another combination ambulance cot mattress and patient restraining device constructed according to the principles of the present invention and suitable for use on the ambulance cot of FIG. 5.
Figure 13:
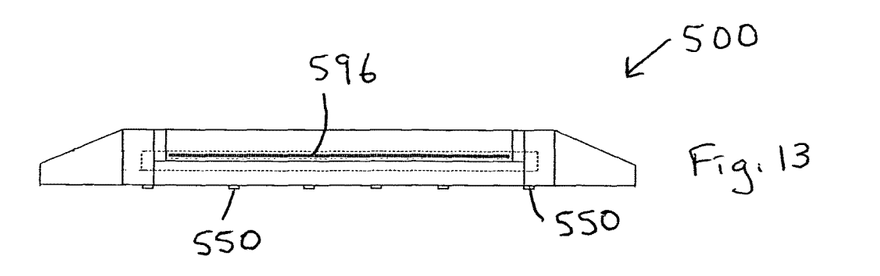
FIG. 13 is a side view of the combination of FIG. 12.
Figure 14:
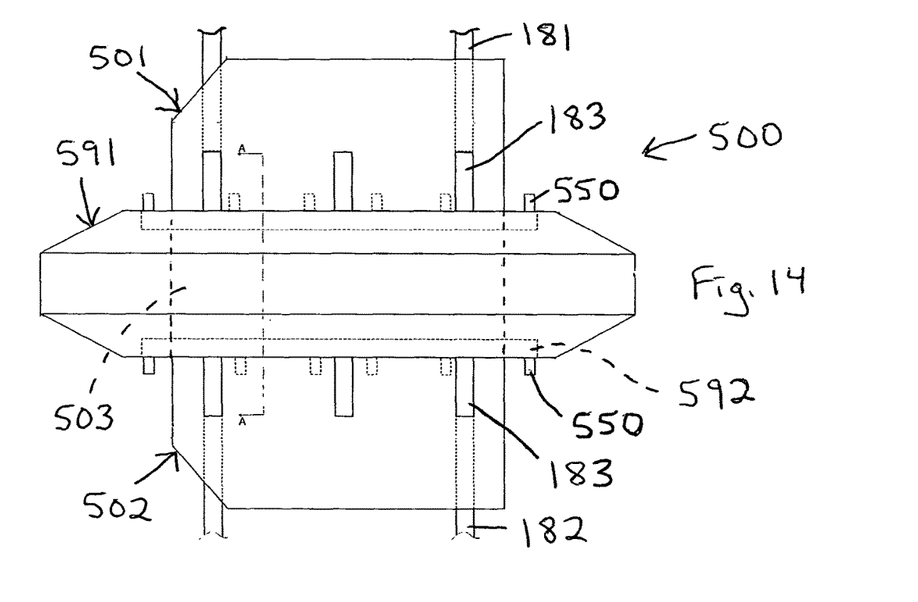
FIG. 14 is a bottom view of the combination of FIG. 12.

Six looped anchor straps 550 project outward from each side of the mattress 591. As shown in FIG. 12, these straps 550 are disposed proximate the ambulance cot rail 94' when the mattress 591 is resting on a conventional ambulance cot. Separate straps 99 are connected in series between opposite side straps 550 to anchor the mattress 591 on the cot. The straps 99 are inserted through the loops 550 and then formed into a loop themselves using one or more conventional buckle members.

Each restraint 501 and 502 has a first end portion secured in place inside the mattress 591. On the depicted embodiment 500, an intermediate panel or sheet 503 is secured within the mattress 591 (by sewing to other components of the mattress 591), and opposite left and right sides of the sheet 503 are secured to the first end portions of respective restraints 501 and 502. As a result, the restraints 501 and 502 do not require or have any sort of anchor straps to fasten to the cot. In other words, when a need for the restraints 501 and 502 arises, a user simply unzips the zippers 596 and unfurls the restraints 501 and 502. If deemed necessary, anchor straps could be provided on the restraints 501 and 502 and secured to the cot subsequent to unfurling and prior to loading the patient onto the cot.

Each restraint 501 and 502 has an intermediate portion extending through a respective cavity 592, from the first end portion that is connected to the intermediate member 503, to an opposite second end portion that is selectively deployed outside the respective cavity 592. At least the intermediate portions and the second end portions of the restraints 501 and 502 have respective connector straps 181 and 182 and reinforcing straps 183 that operate in the same manner as those described above and/or incorporated herein by reference to secure the fabric sheets about the patient.

The present invention may also be described in terms of various methods, including, for example, a method of restraining a person relative to an ambulance cot. Such a method may involve (a) providing an ambulance cot having a frame, an ambulance cot mattress mounted on the frame, and at least one restraining member secured to the mattress, wherein the restraining member comprises a sheet of fabric, and connectors secured to the sheet of fabric; (b) selectively storing the restraining member in a cavity defined by the mattress; (c) selectively unfurling the restraining member from the cavity; (d) arranging a person to lie on the mattress; (e) positioning the sheet of fabric about at least the abdomen of the person; (f) securing the connectors into a closed loop that forms a restraint about the person, thereby stabilizing at least the abdomen of the person relative to the frame.

Certain embodiments of the present invention have been disclosed with the understanding that additional embodiments may be derived from this disclosure without departing from the scope of the present invention. For example, with the exception of complementary buckle members, the device 100 is symmetrical about a center line S, but the present invention is not limited to such an arrangement. On an alternative embodiment, the fabric may be arranged to extend from only one side of the patient supporting structure, and to be secured to the opposing side by any of the methods disclosed herein, or by suitable alternative methods. Also, various features of the above-described embodiments may be mixed and matched to arrive at additional alternative embodiments. For examples, buckles on one embodiment may be substituted for Velcro fasteners on another embodiment, and vice versa.

In conclusion, recognizing that this disclosure will enable persons skilled in the art to derive various modifications, improvements, and/or applications that nonetheless embody the essence of the invention, the scope of the present invention is to be limited only to the extent of the following claims.

What is claimed is:

1. An ambulance cot mattress, comprising:
a mattress body having an exterior patient engaging mattress surface that faces upward when the mattress body occupies an operative position;
an outwardly opening storage cavity defined by the mattress body vertically beneath the mattress surface when the mattress body occupies the operative position;
a patient restraint having a first end portion secured inside the mattress body, an intermediate portion extending through the cavity, and an opposite second end portion alternatively stored inside the cavity and deployed outside the cavity, wherein at least the second end portion comprises (a) a sheet of fabric, and (b) connector straps secured to the sheet of fabric, and when in use with the mattress body in the operative position, the second end portion extends out from the cavity and over at least a portion of the mattress body, and when stored inside the cavity with the mattress body in the operative position, the second end portion occupies space vertically beneath the mattress surface; and
wherein when the mattress body occupies the operative position, the cavity is disposed along a side of the mattress body, and mattress padding vertically overlaps the cavity.

2. The mattress of claim 1, further comprising a zipper sewn into the mattress body along an edge of the cavity, wherein the zipper is operable to open and close the cavity.

3. The mattress of claim 1, wherein a zipper extends along an outboard edge of the cavity, opposite mattress padding that is inboard of the cavity, to provide selective access to the cavity.

4. The mattress of claim 1, wherein the connector straps extend laterally across the sheet of fabric at respective, longitudinally spaced locations along the sheet of fabric.

5. The mattress of claim 1, further comprising mattress padding disposed inside the mattress body in a manner that vertically overlaps the cavity when the mattress body occupies the operative position.

6. The mattress of claim 5, further comprising mattress padding disposed inside the mattress body in a manner that vertically underlies the cavity when the mattress body occupies the operative position.

7. The mattress of claim 1, wherein in the operative position, the mattress body has left and right sides that extend to a first elevation, and a middle section disposed therebetween that extends to a second elevation, and the first elevation is higher than the second elevation to accommodate at least one said cavity in at least one of the sides.

8. An ambulance cot mattress, comprising:
a mattress body extending longitudinally from a head end to a foot end, and laterally from a left side to a right side, wherein the mattress body defines (a) an upwardly facing body supporting surface; (b) an outwardly opening left storage cavity extending laterally into the left side of the mattress body; and (c) an outwardly opening right storage cavity extending laterally into the right side of the mattress body;
a left side patient restraint having a first end portion secured inside the mattress body at a location vertically beneath the body supporting surface, and an opposite second end portion; and
a right side patient restraint having a first end portion secured inside the mattress body at a location vertically beneath the body supporting surface, and an opposite second end portion, wherein each said second end portion comprises at least (a) a sheet of fabric, and (b) connector straps secured to the sheet of fabric, and each said second end portion is selectively stored inside a respective said cavity when not in use, and extends out from the respective said cavity and over at least a portion of the body supporting surface when in use;
wherein the first end portion of each said restraint is secured to the mattress body inboard of each said cavity; and
wherein each said cavity is vertically overlapped by mattress padding disposed inside the mattress body.

9. The ambulance cot mattress of claim 8, wherein an intermediate member is interconnected in series between the first end portion of the left side patient restraint and the first end portion of the right side patient restraint at a location beneath the body supporting surface.

10. The ambulance cot mattress of claim 8, wherein in an operative mode, the connector straps on the left side patient restraint are selectively connected to the connector straps on the right side patient restraint to form a closed loop about a person lying on the mattress and beneath each said sheet of fabric.

11. The ambulance cot mattress of claim 8, wherein each said cavity is selectively accessible via a respective zipper extending along a respective said side of the mattress body.

12. The ambulance cot mattress of claim 8, wherein the first end portion of the left side patient restraint and the first end portion of the right side patient restraint are integral portions of a single strap that extends through the mattress body.

13. The ambulance cot mattress of claim 8, wherein the left side patient restraint and the right side patient restraint are interconnected by at least one member that extends through the mattress body between the left side cavity and the right side cavity.

14. An ambulance cot mattress for transporting a patient, comprising:
   a mattress body extending longitudinally from a head end to a foot end, and laterally from a left side to a right side, wherein the mattress body defines (a) an upwardly facing body supporting surface defining a perimeter; and (b) at least one storage cavity disposed (i) under the body supporting surface and (ii) inside a vertical projection of the perimeter; and
   at least one patient restraint having a first end portion secured inside said at least one storage cavity, and an opposite second end portion extending out from said at least one storage cavity and cooperating with the body supporting surface to form a closed loop about the patient; and
   wherein said at least one storage cavity includes a left side cavity disposed along the left side of the mattress, and mattress padding is disposed vertically between the left side cavity and the body supporting surface, and horizontally between the left side cavity and the right side of the mattress body.

15. The mattress of claim 14, wherein additional mattress padding is disposed vertically beneath the left side cavity.

16. The mattress of claim 14, wherein the mattress body is taller in height along at least one said side to accommodate said at least one cavity, and shorter in height along a middle section disposed therebetween.

* * * * *